United States Patent
Heath

(10) Patent No.: US 8,097,791 B2
(45) Date of Patent: Jan. 17, 2012

(54) TOMATO LINE FDR 15-2081

(75) Inventor: Douglas Heath, Rocklin, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 139 days.

(21) Appl. No.: 12/718,644

(22) Filed: Mar. 5, 2010

(65) Prior Publication Data

US 2011/0219472 A1    Sep. 8, 2011

(51) Int. Cl.
*A01H 1/00* (2006.01)
*C07H 21/04* (2006.01)
*C07K 14/415* (2006.01)
*C12N 15/00* (2006.01)

(52) U.S. Cl. ............ 800/317.4; 435/468; 435/411; 435/418; 435/419; 530/370; 536/23.1; 536/23.6; 800/260; 800/278; 800/300; 800/301; 800/302

(58) Field of Classification Search ............ 435/411, 435/468; 530/370; 536/23.6; 800/317.4; Plt./261
See application file for complete search history.

(56) References Cited

U.S. PATENT DOCUMENTS

| | | | |
|---|---|---|---|
| 2007/0180572 A1* | 8/2007 | Fernandez | 800/317.4 |
| 2009/0255010 A1 | 10/2009 | Ramon | |

OTHER PUBLICATIONS

U.S. Appl. No. 12/709,024, filed Feb. 19, 2010, Heath.
U.S. Appl. No. 12/709,036, filed Feb. 19, 2010, Heath.
U.S. Appl. No. 12/817,199, filed Jun. 16, 2010, Fowler et al.
Certificate on the Grant of Community Plant Variety Rights for Tomato Variety (*Lycopersicon lycopersicum* L. Karsten) FDR152078, dated Dec. 4, 2006, European Union.
Draft Mexican Application for Plant Variety Protection for Tomato Variety (*Lycopersicon lycopersicum* L. Karsten) FDR 15-2078, dated Jul. 2, 2007.
Draft Mexican Application for Plant Variety Protection for Tomato Variety (*Lycopersicon lycopersicum* L. Karsten) FDR 15-2078, dated Jul. 2, 2007 (English).
Certificate on the Grant of Community Plant Variety Rights, for Tomato Variety (*Lycopersicon lycopersicum* L. Karsten) FDR162045, dated Sep. 24, 2001, European Union.
Draft Mexican Application for Plant Variety Protection for Tomato Variety (*Lycopersicon lycopersicum* L. Karsten) FDR 16-2045, dated Jul. 18, 2006.
Draft Mexican Application for Plant Variety Protection for Tomato Variety (*Lycopersicon lycopersicum* L. Karsten) FDR 16-2045, dated Jul. 18, 2006. (English).
Mexican Title of Breeder for Tomato Variety (*Lycopersicon lycopersicum*) FDR 162045, dated Jun. 21, 2010.
Mexican Title of Breeder for Tomato Variety (*Lycopersicon lycopersicum*) FDR 162045, dated Jun. 21, 2010. (English).
Turkish Registration No. 2007/016 for Tomato Variety (*Lycopersicon lycopersicum* L.) FDR 16/2045, dated Jan. 7, 2005.
Turkish Registration No. 2007/016 for Tomato Variety (*Lycopersicon lycopersicum* L.) FDR 16/2045, dated Jan. 7, 2005. (English).

\* cited by examiner

*Primary Examiner* — Phuong Bui
(74) *Attorney, Agent, or Firm* — SNR Denton US LLP; Alissa Eagle, Esq.

(57) ABSTRACT

The invention provides seed and plants of tomato hybrid PS 01565172 and the parent lines thereof. The invention thus relates to the plants, seeds and tissue cultures of tomato hybrid PS 01565172 and the parent lines thereof, and to methods for producing a tomato plant produced by crossing such plants with themselves or with another tomato plant, such as a plant of another genotype. The invention further relates to seeds and plants produced by such crossing. The invention further relates to parts of such plants, including the fruit and gametes of such plants.

29 Claims, No Drawings

TOMATO LINE FDR 15-2081

FIELD OF THE INVENTION

The present invention relates to the field of plant breeding and, more specifically, to the development of tomato hybrid PS 01565172 and the inbred tomato lines FDR 15-2081 and FDS 15-2118.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

SUMMARY OF THE INVENTION

In one aspect, the present invention provides a tomato plant of the hybrid designated PS 01565172, the tomato line FDR 15-2081 or tomato line FDS 15-2118. Also provided are tomato plants having all the physiological and morphological characteristics of such a plant. Parts of these tomato plants are also provided, for example, including pollen, an ovule, scion, a rootstock, a fruit, and a cell of the plant.

In another aspect of the invention, a plant of tomato hybrid PS 01565172 and/or tomato lines FDR 15-2081 and FDS 15-2118 comprising an added heritable trait is provided. The heritable trait may comprise a genetic locus that is, for example, a dominant or recessive allele. In one embodiment of the invention, a plant of tomato hybrid PS 01565172 and/or tomato lines FDR 15-2081 and FDS 15-2118 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The invention also concerns the seed of tomato hybrid PS 01565172 and/or tomato lines FDR 15-2081 and FDS 15-2118. The tomato seed of the invention may be provided as an essentially homogeneous population of tomato seed of tomato hybrid PS 01565172 and/or tomato lines FDR 15-2081 and FDS 15-2118. Essentially homogeneous populations of seed are generally free from substantial numbers of other seed. Therefore, seed of hybrid PS 01565172 and/or tomato lines FDR 15-2081 and FDS 15-2118 may be defined as forming at least about 97% of the total seed, including at least about 98%, 99% or more of the seed. The seed population may be separately grown to provide an essentially homogeneous population of tomato plants designated PS 01565172 and/or tomato lines FDR 15-2081 and FDS 15-2118.

In yet another aspect of the invention, a tissue culture of regenerable cells of a tomato plant of hybrid PS 01565172 and/or tomato lines FDR 15-2081 and FDS 15-2118 is provided. The tissue culture will preferably be capable of regenerating tomato plants capable of expressing all of the physiological and morphological characteristics of the starting plant, and of regenerating plants having substantially the same genotype as the starting plant. Examples of some of the physiological and morphological characteristics of the hybrid PS 01565172 and/or tomato lines FDR 15-2081 and FDS 15-2118 include those traits set forth in the tables herein. The regenerable cells in such tissue cultures may be derived, for example, from embryos, meristems, cotyledons, pollen, leaves, anthers, roots, root tips, pistils, flowers, seed and stalks. Still further, the present invention provides tomato plants regenerated from a tissue culture of the invention, the plants having all the physiological and morphological characteristics of hybrid PS 01565172 and/or tomato lines FDR 15-2081 and FDS 15-2118.

In still yet another aspect of the invention, processes are provided for producing tomato seeds, plants and fruit, which processes generally comprise crossing a first parent tomato plant with a second parent tomato plant, wherein at least one of the first or second parent tomato plants is a plant of tomato line FDR 15-2081 or tomato line FDS 15-2118. These processes may be further exemplified as processes for preparing hybrid tomato seed or plants, wherein a first tomato plant is crossed with a second tomato plant of a different, distinct genotype to provide a hybrid that has, as one of its parents, a plant of tomato line FDR 15-2081 or tomato line FDS 15-2118. In these processes, crossing will result in the production of seed. The seed production occurs regardless of whether the seed is collected or not.

In one embodiment of the invention, the first step in "crossing" comprises planting seeds of a first and second parent tomato plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent tomato plants into plants that bear flowers. A third step may comprise preventing self-pollination of the plants, such as by emasculating the flowers (i.e., killing or removing the pollen).

A fourth step for a hybrid cross may comprise cross-pollination between the first and second parent tomato plants. Yet another step comprises harvesting the seeds from at least one of the parent tomato plants. The harvested seed can be grown to produce a tomato plant or hybrid tomato plant.

The present invention also provides the tomato seeds and plants produced by a process that comprises crossing a first parent tomato plant with a second parent tomato plant, wherein at least one of the first or second parent tomato plants is a plant of tomato hybrid PS 01565172 and/or tomato lines FDR 15-2081 and FDS 15-2118. In one embodiment of the invention, tomato seed and plants produced by the process are first generation ($F_1$) hybrid tomato seed and plants produced by crossing a plant in accordance with the invention with another, distinct plant. The present invention further contemplates plant parts of such an $F_1$ hybrid tomato plant, and methods of use thereof. Therefore, certain exemplary embodiments of the invention provide an $F_1$ hybrid tomato plant and seed thereof.

In still yet another aspect, the present invention provides a method of producing a plant derived from hybrid PS 01565172 and/or tomato lines FDR 15-2081 and FDS 15-2118, the method comprising the steps of: (a) preparing a progeny plant derived from hybrid PS 01565172 and/or tomato lines FDR 15-2081 and FDS 15-2118, wherein said preparing comprises crossing a plant of the hybrid PS 01565172 and/or tomato lines FDR 15-2081 and FDS 15-2118 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid PS 01565172 and/or tomato lines FDR 15-2081 and FDS 15-2118. The plant derived from hybrid PS 01565172 and/or tomato lines FDR 15-2081 and FDS 15-2118 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid PS 01565172 and/or tomato lines FDR 15-2081 and FDS 15-2118 is obtained which possesses some of the desirable traits of the line/hybrid as well as potentially other selected traits.

In certain embodiments, the present invention provides a method of producing food or feed comprising: (a) obtaining a plant of tomato hybrid PS 01565172 and/or tomato lines FDR 15-2081 and FDS 15-2118, wherein the plant has been cultivated to maturity, and (b) collecting at least one tomato from the plant.

In still yet another aspect of the invention, the genetic complement of tomato hybrid PS 01565172 and/or tomato lines FDR 15-2081 and FDS 15-2118 is provided. The phrase "genetic complement" is used to refer to the aggregate of nucleotide sequences, the expression of which sequences defines the phenotype of, in the present case, a tomato plant, or a cell or tissue of that plant. A genetic complement thus represents the genetic makeup of a cell, tissue or plant, and a hybrid genetic complement represents the genetic make up of a hybrid cell, tissue or plant. The invention thus provides tomato plant cells that have a genetic complement in accordance with the tomato plant cells disclosed herein, and seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid PS 01565172 and/or tomato lines FDR 15-2081 and FDS 15-2118 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by tomato plant cells, tissues, plants, and seeds, formed by the combination of a haploid genetic complement of a tomato plant of the invention with a haploid genetic complement of a second tomato plant, preferably, another, distinct tomato plant. In another aspect, the present invention provides a tomato plant regenerated from a tissue culture that comprises a hybrid genetic complement of this invention.

In still yet another aspect, the invention provides a plant of an hybrid tomato that exhibits a combination of traits comprising: a high-quality saladette tomato with a classic egg shape; uniform large fruits; excellent fruit set; resistance to tomato spotted wilt virus; resistance to tomato yellow leaf curl virus; resistance to nematodes; and resistance to tomato marichitez virus (which is also known as tomato apical necrosis virus). In certain embodiments, the combination of traits may be defined as controlled by genetic means for the expression of the combination of traits found in tomato hybrid PS 01565172.

In still yet another aspect, the invention provides a method of determining the genotype of a plant of tomato hybrid PS 01565172 and/or tomato lines FDR 15-2081 and FDS 15-2118 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of tomato hybrid PS 01565172, tomato line FDR 15-2081 and tomato line FDS 15-2118. The hybrid PS 01565172 is produced by the cross of parent lines FDR 15-2081 and FDS 15-2118. The parent lines show uniformity and stability within the limits of environmental influence. By crossing the parent lines, uniform seed hybrid PS 01565172 can be obtained.

The development of tomato hybrid PS 01565172 and its parent lines can be summarized as follows.

A. Origin and Breeding History of Tomato Hybrid PS 01565172

The parents of hybrid PS 01565172 are FDR 15-2081 and FDS 15-2118. These parents were created as follows:

FDR 15-2081 was derived from FDR 15-2045 and FL 7547. FDR 15-2045 produces extra-large fruit, a trait derived from NC 84173. FL 7547 provided resistance to *Fusarium* wilt, race 3.

FDS 15-2118 bears pear-shaped fruit and was derived from the Seminis proprietary hybrid Xaman. Xaman carries resistance to tomato spotted wilt virus and tomato yellow leaf curl virus. Xaman is derived from FDR 15-2078 and FDS 15-2058.

The combination of the parents FDR 15-2081 and FDS 15-2118 provides hybrid PS 0156172 with resistance to tomato marchitez virus. Tomato marchitez virus is also known as tomato apical necrosis virus. The parent lines are uniform and stable, as is a hybrid therefrom. A small percentage of variants can occur within commercially acceptable limits for almost any characteristic during the course of repeated multiplication. However no variants are expected.

B. Physiological and Morphological Characteristics of Tomato Hybrid PS 01565172, Tomato Line FDR 15-2081 and Tomato Line FDS 15-2118

In accordance with one aspect of the present invention, there is provided a plant having the physiological and morphological characteristics of tomato hybrid PS 01565172 and the parent lines thereof. A description of the physiological and morphological characteristics of such plants is presented in Tables 1-3.

TABLE 1

Physiological and Morphological Characteristics of Hybrid PS 01565172

| CHARACTERISTIC | PS 01565172 | Picus |
|---|---|---|
| 1. Seedling | | |
| Anthocyanin in hypocotyl of 2-15 cm seedling | Present (Montfavet H 63.4) | Present |
| Habit of 3-4 week old seedling | Normal | Normal |
| 2. Mature plant | | |
| Plant height | 60 cm | 69 cm |
| Growth type | Determinate (Campbell 1327, Prisca) | Determinate |
| Number of inflorescences on main stem (side shoots to be removed) | Medium (Montfavet H 63.4) | Medium |
| Form | Lax, open | Lax, open |
| Size of canopy (compared to others of similar type) | Medium | Large |
| Habit | Sprawling (decumbent) | Sprawling |
| 3. Stem | | |
| Anthocyanin coloration of upper third | Weak (Montfavet H 63.5) | Absent or very weak |
| Branching | Intermediate (Westover) | Profuse |
| Branching at cotyledon or first leafy node | Absent | Present |
| Number of nodes between first inflorescence | 4 to 7 | 7 to 10 |
| Number of nodes between early (1st to 2nd, 2nd to 3rd) inflorescences | 1 to 4 | 1 to 4 |
| Number of nodes between later developing inflorescences | 1 to 4 | 1 to 4 |
| Pubescence on younger stems | Moderately hairy | Moderately hairy |
| 4. Leaf | | |
| Type (mature leaf beneath the 3rd inflorescence) | Tomato | Tomato |
| Morphology (mature leaf beneath the 3rd inflorescence) | Bipinnate | Bipinnate |
| Margins of major leaflets (mature leaf beneath the 3rd inflorescence) | Shallowly toothed or scalloped | Shallowly toothed or scalloped |
| Marginal rolling or wiltiness (mature leaf beneath the 3rd inflorescence) | Absent | Absent |
| Onset of leaflet rolling (mature leaf | Late season | Mid season |

TABLE 1-continued

Physiological and Morphological Characteristics of Hybrid PS 01565172

| CHARACTERISTIC | PS 01565172 | Picus |
|---|---|---|
| beneath the 3rd inflorescence) | | |
| Surface of major leaflets (mature leaf beneath the 3rd inflorescence) | Smooth | Smooth |
| Pubescence (mature leaf beneath the 3rd inflorescence) | Normal | Hirsute |
| Attitude (in middle third of plant) | Semi-erect (Allround, Drakar, Vitador) | Horizontal |
| Length | Medium (Lorena) | Long |
| Width | Medium | Medium |
| Division of blade | Pinnate (Mikado, Pilot, Red Jacket) | Pinnate |
| Size of leaflets (in middle of leaf) | Large (Daniela, Hynema) | Large |
| Intensity of green color | Medium (Lucy) | Dark |
| Glossiness (in middle third of plant) | Weak (Daniela) | Weak |
| Attitude of petiole of leaflet in relation to main axis (in middle third of plant) | Semi-drooping Montfavet H 63.5 | Semi drooping |
| 5. Inflorescence | | |
| Type (2nd and 3rd truss) | Mainly uniparous (Dynamo) | Mainly multiparous |
| Type (3rd inflorescence) | Simple | Forked |
| Average number of flowers in inflorescence (3rd inflorescence) | 5 | 6 |
| Leafy or "Running" inflorescence (3rd inflorescence) | Absent | Occasional |
| 6. Flower | | |
| Calyx | Normal (Lobes awl shaped) | Normal |
| Calyx-lobes | Approx. equaling corolla | Shorter than corolla |
| Corolla Color | Yellow | Yellow |
| Style Pubescence | Absent or very scarce (Campbell 1327) | Sparse |
| Anthers | All fused into tube | All fused into tube |
| Fasciation (1st flower of 2nd or 3rd inflorescence) | Absent (Monalbo, Moneymaker) | Occasionally present |
| Color | Yellow (Marmande VR) | Yellow |
| 7. Fruit | | |
| Typical shape in longitudinal section (3rd fruit of 2nd or 3rd cluster) | Elliptical | Heart Shaped |
| Shape of transverse/cross section (3rd fruit of 2nd or 3rd cluster) | Round | Round |
| Shape of stem end (3rd fruit of 2nd or 3rd cluster) | Indented | Flat |
| Shape of blossom end (3rd fruit of 2nd or 3rd cluster) | Pointed/tapered (Europeel, Heinze 1706, Hypeel 244, Roma VF) | Flat to pointed/ nippled |
| Size of blossom scar | Small (Montfavet H 63.4, Montfavet 63.5) | Very small |
| Shape of pistil scar (3rd fruit of 2nd or 3rd cluster) | Dot | Dot |
| Peduncle: abscission layer (3rd fruit of 2nd or 3rd cluster) | Present (Pedicellate) (Montfavet H 63.5, Roma) | Present |
| Peduncle: length (from abscission layer to calyx) | Medium (Dario, Primosol) | Medium |
| Ribbing at peduncle end | Weak (Early Mech, Hypeel 244, Melody, Peto Gro, Rio Grande) | Absent or very weak |
| Depression at peduncle end | Weak (Futuria, Melody) | Weak |
| Size of stem/peduncle scar | Medium (Montfavet H 63.4, Montfavet 63.5, Rutgers) | Small |

TABLE 1-continued

Physiological and Morphological Characteristics of Hybrid PS 01565172

| CHARACTERISTIC | PS 01565172 | Picus |
|---|---|---|
| Point of detachment of fruit at harvest (3rd fruit of 2nd or 3rd cluster) | At pedicel joint | At calyx attachement |
| Length of dedicel (from joint to calyz attachment, 3rd fruit of 2nd or 3rd cluster) | 11 mm | 13 mm |
| Length of mature fruit (3rd fruit of 2nd or 3rd cluster) | 67 mm | 79 mm |
| Diameter of fruit at widest point (stem axis, 3rd fruit of 2nd or 3rd cluster) | 53 mm | 46 mm |
| Weight of mature fruit (3rd fruit of 2nd or 3rd cluster) | 96 grams | 105 gm |
| Size | Medium (Alphamec, Diego) | Medium |
| Ratio length/diameter | Medium (Early Mech, Peto Gro) | Medium |
| Core | Present | Coreless |
| Size of core in cross section (in relation to total diameter) | Medium (Montfavet H 63.4, Montfavet H 63.5) | |
| Number of locules | 3 or 4 (Montfavet H 63.5) | 2 or 3 |
| Surface | Smooth | Smooth |
| Base color (mature-green stage) | Light Green (Lanai, VF 145-F5) | Apple or medium green |
| Pattern (mature-green stage) | Uniform green | Green shouldered |
| Green shoulder (before maturity) | Absent (Felicia, Rio Grande, Trust) | Present |
| Shoulder color if different from base | | Yellow green |
| Extent of green shoulder (before maturity) | | Medium |
| Intensity of green color of shoulder (before maturity) | | Medium |
| Intensity of green color of fruit (before maturity) | Light (Capello, Duranto, Trust) | Medium |
| Color at maturity (full-ripe) | Red (Ferline, Daniela, Montfavet H 63.5) | Red |
| Color of flesh at maturity (full-ripe) | Red/Crimson (Forline, Saint-Pierre) | Red/Crimson |
| Flesh color | Uniform | Uniform |
| Locular gel color of table-ripe fruit | Red | Red |
| Firmness | Firm (Fernova, Konsul, Tradiro) | Medium |
| Shelf life | Long (Daniela) | Long |
| Time of flowering | Early (Feria, Primabel) | Medium |
| Time of maturity | Early (Feria, Rossol) | Very early |
| Ripening (blossom-to-stem axis) | Uniform | Blossom to stem end |
| Ripening (radial axis) | Uniform | Uniform |
| Epidermis color | Yellow | Yellow |
| Epidermis | Normal | Normal |
| Epidermis Texture | Tough | Tough |
| Thickness of pericarp | Thick (Cal J, Daniela, Ferline, Peto Gro, Rio Grande) | Thick |
| Sensitivity to silvering | Insensitive (Marathon, Sano) | Insensitive |
| 8. Chemistry and composition of full-ripe fruits | | |
| pH | 4.5 | 4.36 |
| Titratable acidity, as % citric | 0.22112 | 0.40672 |
| Total solids (dry matter, seeds and skin removed) | 5.600594 grams per 100 grams of sample | 5.27936 grams per 100 grams of sample |
| Soluble solids as °Brix | 4.99 | 4.595 |

TABLE 1-continued

Physiological and Morphological Characteristics of Hybrid PS 01565172

| CHARACTERISTIC | PS 01565172 | Picus |
|---|---|---|
| 9. Phenology | | |
| Seeding to once over harvest | 107 days | 72 days |
| Fruiting season | Long (Marglobe) | Long |
| Relative maturity in areas tested | Early | Early |
| 10. Adaptation | | |
| Culture | Field | Field |
| Principle use | Fresh Market | Fresh Market |
| Machine Harvest | Not adapted | Not adapted |
| Regions to which adaptation has been demonstrated | Sacramento and Upper San Joaquin Valley of California | |

*These are typical values. Values may vary due to environment. Other values that are substantially equivalent are also within the scope of the invention.

TABLE 2

Physiological and Morphological Characteristics of Line FDR 15-2081

| CHARACTERISTIC | FDR 15-2081 | FDR 15-478*HP478 (FLA 7060) |
|---|---|---|
| 1. Seedling | | |
| Anthocyanin in hypocotyl of 2-15 cm seedling | Present (Montfavet H 63.4) | Present |
| Habit of 3-4 week old seedling | Normal | Normal |
| 2. Mature plant | | |
| Plant Height | 55.7 cm | 55 cm |
| Growth type | Determinate (Campbell 1327, Prisca) | Determinate |
| Number of inflorescences on main stem (side shoots to be removed) | Medium (Montfavet H 63.4) | Medium |
| Form | Normal | Normal |
| Size of canopy (compared to others of similar type) | Medium | Medium |
| Habit | Semi-erect | Semi-erect |
| 3. Stem | | |
| Anthocyanin coloration of upper third | Absent or very weak | Medium |
| Branching | Intermediate (Westover) | Intermediate |
| Branching at cotyledon or first leafy node | Present | Present |
| Number of nodes between first inflorescence | 7 to 10 | 7 to 10 |
| Number of nodes between early (1st to 2nd, 2nd to 3rd) inflorescences | 1 to 4 | 1 to 4 |
| Number of nodes between later developing inflorescences | 1 to 4 | 1 to 4 |
| Pubescence on younger stems | Sparsely hairy (scattered long hairs) | Sparsely hairy |
| 4. Leaf | | |
| Type (mature leaf beneath the 3rd inflorescence) | Tomato | Tomato |
| Morphology (Mature leaf beneath the 3rd Inflorescence) | Bipinnate | Bipinnate |
| Margins of major leaflets (mature leaf beneath the 3rd inflorescence) | Shallowly toothed or scalloped | Shallowly toothed or scalloped |
| Marginal rolling or wiltiness (mature leaf beneath the 3rd inflorescence) | Strong | Absent |
| Onset of leaflet rolling (mature leaf beneath the 3rd inflorescence) | Mid season | Late season |
| Surface of major leaflets (mature leaf beneath the 3rd inflorescence) | Rugose (bumpy or veiny) | Rugose |
| Pubescence (mature leaf beneath the 3rd inflorescence) | Normal | Hirsute |
| Attitude (in middle third of plant) | Semi-erect (Allround, Drakar, Vitador) | Semi Drooping |
| Length | Medium (Lorena) | Medium |

TABLE 2-continued

Physiological and Morphological Characteristics of Line FDR 15-2081

| CHARACTERISTIC | FDR 15-2081 | FDR 15-478*HP478 (FLA 7060) |
|---|---|---|
| Width | Medium | Medium |
| Division of blade | Pinnate (Mikado, Pilot, Red Jacket) | Pinnate |
| Size of leaflets (in middle of leaf) | Medium (Marmande VR, Royesta) | Medium |
| Intensity of green color | Medium (Lucy) | Medium |
| Glossiness (in middle third of plant) | Weak (Daniela) | Medium |
| Blistering (in middle third of plant) | | Weak |
| Size of blisters (in middle third of plant) | | Small |
| Attitude of petiole of leaflet in relation to main axis (in middle third of plant) | Horizontal (Sonatine) | Semi drooping |
| 5. Inflorescence | | |
| Type (2nd and 3rd truss) | Mainly uniparous (Dynamo) | Mainly uniparous |
| Type (3rd inflorescence) | Simple | Simple |
| Average number of flowers in inflorescence (3rd inflorescence) | 4.8 | 4 |
| Leafy or "Running" inflorescence (3rd inflorescence) | Occasional | Occasional |
| 6. Flower | | |
| Calyx | Normal (lobes awl shaped) | Normal |
| Calyx-lobes | Shorter than corolla | Shorter than corolla |
| Corolla Color | Yellow | Yellow |
| Style Pubescence | Absent or very scarce (Campbell 1327) | Sparse |
| Anthers | All fused into tube | All fused into tube |
| Fasciation (1st flower of 2nd or 3rd inflorescence) | Absent (Monalbo, Moneymaker) | Absent |
| Color | Yellow (Marmande VR) | Yellow |
| 7. Fruit | | |
| Typical shape in longitudinal section (3rd fruit of 2nd or 3rd cluster) | Circular | Circular |
| Shape of transverse/cross section (3rd fruit of 2nd or 3rd cluster) | Round | Round |
| Shape of stem end (3rd fruit of 2nd or 3rd cluster) | Indented | Indented |
| Shape of blossom end (3rd fruit of 2nd or 3rd cluster) | Indented to flat | Flat |
| Size of blossom scar | | Medium |
| Shape of pistil scar (3rd fruit of 2nd or 3rd cluster) | Dot | Irregular |
| Peduncle: abscission layer (3rd fruit of 2nd or 3rd cluster) | Present (pedicellate) (Montfavet H 63.5, Roma) | Present |
| Peduncle: length (from abscission layer to calyx) | Short (Cerise, Ferline, Montfavet H 63.18, Rossol) | Long |
| Ribbing at peduncle end | Absent or very weak (Calimero, Cerise) | Weak |
| Depression at peduncle end | Weak (Futuria, Melody) | Weak |
| Size of stem/peduncle scar | Medium (Montfavet H 63.4, Montfavet H 63.5, Rutgers) | Large |
| Point of detachment of fruit at harvest (3rd fruit of 2nd or 3rd cluster) | At pedicel joint | At pedicel joint |
| Length of dedicel from joint to calyx attachment (3rd fruit of 2nd or 3rd cluster) | 9.7 mm | 16 mm |
| Length of mature fruit (stem axis, 3rd fruit of 2nd or 3rd cluster) | 51.7 mm | 69 mm |

TABLE 2-continued

Physiological and Morphological Characteristics of Line FDR 15-2081

| CHARACTERISTIC | FDR 15-2081 | FDR 15-478*HP478 (FLA 7060) |
|---|---|---|
| Diameter of fruit at widest point (3rd fruit of 2nd or 3rd cluster) | 61.3 mm | 75 mm |
| Weight of mature fruit (3rd fruit of 2nd or 3rd cluster) | 120.2 grams | 234 grams |
| Size | Large (Carmello, Ringo) | Large |
| Ratio length/diameter | Small (Alicia) | Large |
| Core | Coreless (absent or smaller than 6 × 6 mm) | Coreless |
| Number of locules | Only 2 (Early Mech, Europeel, San Marzano) | 4, 5 or 6 |
| Surface | Smooth | Smooth |
| Base color (mature-green stage) | Light green (Lanai, VF 145-F5) | Yellow green |
| Pattern (mature-green stage) | Uniform green | Radial stripes on sides of fruit |
| Green shoulder (before maturity) | Present (Daniela, Montfavet H 63.5) | Absent |
| Shoulder color if different from base | Yellow green | |
| Extent of green shoulder (before maturity) | Medium (Erlidor, Foxy, Montfavet H 63.5) | |
| Intensity of green color of shoulder (before maturity) | Light (Juboline) | |
| Intensity of green color of fruit (before maturity) | Light (Capello, Duranto, Trust) | Light |
| Color at maturity (full-ripe) | Red (Ferline, Daniela, Montfavet H 63.5) | Red |
| Color of flesh at maturity (full-ripe) | Red/crimson (Ferline, Saint-Pierre) | Red/crimson |
| Flesh color | Uniform | Uniform |
| Locular gel color of table-ripe fruit | Yellow | Red |
| Firmness | Firm (Fernova, Konsul, Tradiro) | Medium |
| Shelf life | Medium (Durinta) | Medium |
| Time of flowering | Medium (Montfavet H 63.5, Prisca) | Medium |
| Time of maturity | Medium (Montfavet H 63.5) | Medium |
| Ripening (blossom-to-stem axis) | Uniform | Blossom to stem end |
| Ripening (radial axis) | Uniform | Uniform |
| Epidermis color | Yellow | Yellow |
| Epidermis | Easy-peel | Normal |
| Epidermis Texture | Tender | Tough |
| Thickness of pericarp | Medium (Carmello, Europeel, Floradade, Heinz 1706, Montfavet H 63.5) | Medium |
| Sensitivity to silvering | Insensitive (Marathon, Sano) | Insensitive |
| 8. Chemistry and composition of full-ripe fruits | | |
| pH | 4.295 | 4.345 |
| Titratable acidity, as % citric | 0.419520004 | 0.51808 |
| Total solids (dry matter, seeds and skin removed) | 5.929212036 grams per 100 grams of sample | 6.815822 grams per 100 grams of sample |
| Soluble solids as °Brix | 5.175 | 6 |
| 9. Phenology | | |
| Seeding to once over harvest | 120 days | 106 days |

TABLE 2-continued

Physiological and Morphological Characteristics of Line FDR 15-2081

| CHARACTERISTIC | FDR 15-2081 | FDR 15-478*HP478 (FLA 7060) |
|---|---|---|
| Fruiting season | Medium (Westover) | Medium |
| Relative maturity in areas tested | Early | Medium early |
| 10. Adaptation | | |
| Culture | Field | Field |
| Principle use | Fresh market | Fresh Market |
| Machine Harvest | Not adapted | Not adapted |
| Regions to which adaptation has been demonstrated | Sacramento and Upper San Joaquin Valley of California | |

*These are typical values. Values may vary due to environment. Other values that are substantially equivalent are also within the scope of the invention.

TABLE 3

Physiological and Morphological Characteristics of Line FDS 15-2118

| CHARACTERISTIC | FDS 15-2118 | Loreto |
|---|---|---|
| 1. Seedling | | |
| Anthocyanin in hypocotyl of 2-15 cm seedling | Present (Montfavet H 63.4) | Present |
| Habit of 3-4 week old seedling | Normal | Normal |
| 2. Mature plant | | |
| Plant Height | 46 cm | 84 cm |
| Growth type | Determinate (Campbell 1327, Prisca) | Determinate |
| Number of inflorescences on main stem (side shoots to be removed) | Medium (Montfavet H 63.4) | Many |
| Form | Lax, open | Open lax |
| Size of canopy | Medium | Large |
| Habit | Sprawling (decumbent) | Sprawling |
| 3. Stem | | |
| Anthocyanin coloration of upper third | Absent or very weak | Absent or very weak |
| Branching | Profuse (UC 82) | Profuse |
| Branching at cotyledon or first leafy node | Present | Present |
| Number of nodes between first inflorescence | 4 to 7 | 7 to 10 |
| Number of nodes between early (1st to 2nd, 2nd to 3rd) inflorescences | 1 to 4 | 1 to 4 |
| Number of nodes between later developing inflorescences | 4 to 7 | 4 to 7 |
| Pubescence on younger stems | Sparsely hairy (scattered long hairs) | Moderately hairy |
| 4. Leaf | | |
| Type (mature leaf beneath the 3rd inflorescence) | Tomato | Tomato |
| Morphology (mature leaf beneath the 3rd Inflorescence) | Bipinnate | Bipinnate |
| Margins of major leaflets (mature leaf beneath the 3rd inflorescence) | Deeply toothed or cut | Shallowly toothed or scalloped |
| Marginal rolling or wiltness (mature leaf beneath the 3rd inflorescence) | Slight | Absent |
| Onset of leaflet rolling (mature leaf beneath the 3rd inflorescence) | Early season | Late season |
| Surface of major leaflets (mature leaf beneath the 3rd inflorescence) | Rugose (bumpy or veiny) | Rugose |
| Pubescence (mature leaf beneath the 3rd inflorescence) | Normal | Hirsute |
| Attitude (in middle third of plant) | Horizontal (Aromata, Triton) | Semi-drooping |
| Length | Medium (Lorena) | Medium |
| Width | Medium | Medium |
| Division of blade | Pinnate (Mikado, Pilot, Red Jacket) | Pinnate |

TABLE 3-continued

Physiological and Morphological Characteristics of Line FDS 15-2118

| CHARACTERISTIC | FDS 15-2118 | Loreto |
|---|---|---|
| Size of leaflets (in middle of leaf) | Small (Tiny Tim) | Medium |
| Intensity of green color | Light (Macero II, Poncette, Rossol) | Dark |
| Glossiness (in middle third of plant) | Weak (Daniela) | Medium |
| Blistering (in middle third of plant) | Weak (Daniela) | |
| Size of blisters (in middle third of plant) | Small (Husky Cherrie Red) | |
| Attitude of petiole of leaflet in relation to main axis (in middle third of plant) | Semi-drooping (Montfavet H 63.5) | Semi-drooping |
| 5. Inflorescence | | |
| Type (2nd and 3rd truss) | Mainly uniparous (Dynamo) | Mainly uniparous |
| Type (3rd inflorescence) | Simple | Simple |
| Average number of flowers in inflorescence (3rd inflorescence) | 5 | 5 |
| Leafy or "Running" inflorescence (3rd inflorescence) | Absent | Occasional |
| 6. Flower | | |
| Calyx | Normal (lobes awl shaped) | Normal |
| Calyx-lobes | Shorter than corolla | Shorter than corolla |
| Corolla Color | Yellow | Yellow |
| Style Pubescence | Absent or very scarce (Campbell 1327) | Sparse |
| Anthers | All fused into tube | All fused into tube |
| Fasciation (1st flower of 2nd or 3rd inflorescence) | Absent (Monalbo, Moneymaker) | Absent |
| Color | Yellow (Marmande VR) | Yellow |
| 7. Fruit | | |
| Typical shape in longitudinal section (3rd fruit of 2nd or 3rd cluster) | Cylindrical | Ovate |
| Shape of transverse/cross section (3rd fruit of 2nd or 3rd cluster) | Round | Round |
| Shape of stem end (3rd fruit of 2nd or 3rd cluster) | Flat | Flat |
| Shape of blossom end (3rd fruit of 2nd or 3rd cluster) | Pointed/tapered (Europeel, Heinz 1706, Hypeel 244, Roma VF) | Indented to flat |
| Size of blossom scar | Small (Montfavet H 63.4, Montfavet H 63.5) | Very small |
| Shape of pistil scar (3rd fruit of 2nd or 3rd cluster) | Dot | Dot |
| Peduncle: abscission layer (3rd fruit of 2nd or 3rd cluster) | Absent (jointless) (Aledo, Bandera, Count, Lerica) | Present |
| Peduncle: length (from abscission layer to calyx) | | Short |
| Ribbing at peduncle end | Absent or very weak (Calimero, Cerise) | Absent or very weak |
| Depression at peduncle end | Absent or very weak (Europeel, Heinz 1706, Rossol, Sweet Baby) | Weak |
| Size of stem/peduncle scar | Very small (Cerise, Heinz 1706, Sweet Baby) | Small |
| Point of detachment of fruit at harvest (3rd fruit of 2nd or 3rd cluster) | At calyx attachment | At calyx attachment |
| Length of dedicel from joint to calyz attachment (3rd fruit of 2nd or 3rd cluster) | 10 mm | 13 mm |
| Length of mature fruit (stem axis, 3rd fruit of 2nd or 3rd cluster) | 97 mm | 62 mm |
| Diameter of fruit at widest point (3rd fruit of 2nd or 3rd cluster) | 43 mm | 49 mm |

TABLE 3-continued

Physiological and Morphological Characteristics of Line FDS 15-2118

| CHARACTERISTIC | FDS 15-2118 | Loreto |
|---|---|---|
| Weight of mature fruit (3rd fruit of 2nd or 3rd cluster) | 90 grams | 90 grams |
| Size | Medium (Alphamech, Diego) | Medium |
| Ratio length/diameter | Medium (Early Mech, Peto Gro) | Medium |
| Core | Coreless (absent or smaller than 6 × 6 mm) | Coreless |
| Number of locules | 2 or 3 (Alphamech, Futuria) | 2 or 3 |
| Surface | Slightly rough | Smooth |
| Base color (mature-green stage) | Light gray-green | Yellow green |
| Pattern (mature-green stage) | Uniform green | Green shouldered |
| Green shoulder (before maturity) | Absent (Felicia, Rio Grande, Trust) | Present |
| Shoulder color if different from base | | Dark green |
| Extent of green shoulder (before maturity) | | Medium |
| Intensity of green color of shoulder (before maturity) | | Medium |
| Intensity of green color of fruit (before maturity) | Light (Capello, Duranto, Trust) | Medium |
| Color at maturity (full-ripe) | Red (Ferline, Daniela, Montfavet H 63.5) | Red |
| Color of flesh at maturity (full-ripe) | Red/crimson (Ferline, Saint-Pierre) | Red crimson |
| Flesh color | Uniform | Uniform |
| Locular gel color of table-ripe fruit | Red | Yellow |
| Firmness | Very firm (Daniela, Karat, Lolek) | Firm |
| Shelf life | Long (Daniela) | Long |
| Time of flowering | Medium (Montfavet H 63.5, Prisca) | Medium |
| Time of maturity | Late (Manific, Saint-Pierre) | Medium |
| Ripening (blossom-to-stem axis) | Uniform | Uniform |
| Ripening (radial axis) | Uniform | Uniform |
| Epidermis color | Yellow | Yellow |
| Epidermis (normal or easy-peel) | Normal | Normal |
| Epidermis Texture | Tough | Average |
| Thickness of pericarp | Medium (Carmello, Europeel, Floradade, Heinz 1706, Montfavet H 63.5) | Medium |
| Sensitivity to silvering | Insensitive (Marathon, Sano) | Insensitive |
| 8. Chemistry and composition of full-ripe fruits | | |
| pH | 4.685 | 4.325 |
| Titratable acidity, as % citric | 0.24416 | 0.39936 |
| Total solids (dry matter, seeds and skin removed) | 5.511496 grams per 100 grams of sample | 5.868482 grams per 100 grams of sample |
| Soluble solids as °Brix | 4.875 | 5.085 |
| 9. Phenology | | |
| Seeding to once over harvest | 107 days | 113 days |
| Fruiting season | Long (Marglobe) | Medium |
| Relative maturity in areas tested | Early | Medium Early |
| 10. Adaptation | | |
| Culture | Field | Field |
| Principle use | Home garden | Fresh market |
| Machine Harvest | | Not adapted |

TABLE 3-continued

Physiological and Morphological Characteristics of Line FDS 15-2118

| CHARACTERISTIC | FDS 15-2118 | Loreto |
|---|---|---|
| Regions to which adaptation has been demonstrated | Sacramento and Upper San Joaquin Valley of California | |

*These are typical values. Values may vary due to environment. Other values that are substantially equivalent are also within the scope of the invention.

C. Breeding Tomato Plants

One aspect of the current invention concerns methods for producing seed of tomato hybrid PS 01565172 involving crossing tomato lines FDR 15-2081 and FDS 15-2118. Alternatively, in other embodiments of the invention, hybrid PS 01565172, line FDR 15-2081, or line FDS 15-2118 may be crossed with itself or with any second plant. Such methods can be used for propagation of hybrid PS 01565172 and/or the tomato lines FDR 15-2081 and FDS 15-2118, or can be used to produce plants that are derived from hybrid PS 01565172 and/or the tomato lines FDR 15-2081 and FDS 15-2118. Plants derived from hybrid PS 01565172 and/or the tomato lines FDR 15-2081 and FDS 15-2118 may be used, in certain embodiments, for the development of new tomato varieties.

The development of new varieties using one or more starting varieties is well known in the art. In accordance with the invention, novel varieties may be created by crossing hybrid PS 01565172 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines based on the elite nature of the genetic background of the plants. In selecting a second plant to cross with PS 01565172 and/or tomato lines FDR 15-2081 and FDS 15-2118 for the purpose of developing novel tomato lines, it will typically be preferred to choose those plants which either themselves exhibit one or more selected desirable characteristics or which exhibit the desired characteristic(s) when in hybrid combination. Examples of desirable traits may include, in specific embodiments, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of tomato plants developed by this invention.

D. Performance Characteristics

As described above, hybrid PS 01565172 exhibits desirable agronomic traits. The performance characteristics of hybrid PS 01565172 were the subject of an objective analysis of the performance traits relative to other varieties. The results of the analysis are presented below.

TABLE 4

Performance Characteristics For Hybrid PS 01565172 and Comparision Hybrids

| Hybrid Name | Average % resistance to tomato marchitez virus | Molecular genotyping results (R = resistant and H = heterozygous [segregating]) |
|---|---|---|
| PS 01565172 | 100 | RR |
| Seri | 100 | RR |
| Yaqui | 70 | RH |
| Veloz | 0 | HH |

E. Further Embodiments of the Invention

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those tomato plants which are developed by a plant breeding technique called backcrossing, wherein essentially all of the morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. The parental tomato plant which contributes the locus for the desired characteristic is termed the nonrecurrent or donor parent. This terminology refers to the fact that the nonrecurrent parent is used one time in the backcross protocol and therefore does not recur. The parental tomato plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a tomato plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny tomato plants of a backcross in which a plant described herein is the recurrent parent comprise (i) the desired trait from the non-recurrent parent and (ii) all of the physiological and morphological characteristics of tomato the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of tomato plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived by Genetic Engineering many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., 1985), including in monocots (see, e.g., Dekeyser et al., 1990; Terada and Shimamoto, 1990); a tandemly duplicated version of the CaMV 35S promoter, the enhanced 35S promoter (P-e35S); 1 the nopaline synthase promoter (An et al., 1988); the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a commelina yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a tomato plant according to the invention. Non-limiting examples of particular genes and corresponding phenotypes one may choose to introduce into a tomato plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a tomato variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tissue Culture: A composition comprising isolated cells of the same or a different type or a collection of such cells organized into parts of a plant.

Transgene: A genetic locus comprising a sequence which has been introduced into the genome of a tomato plant by transformation.

H. Deposit Information

A deposit of tomato hybrid PS 01565172 and inbred parent lines FDR 15-2081 and FDS 15-2118, disclosed above and recited in the claims, has been made with the American Type Culture Collection (ATCC), 10801 University Blvd., Manassas, Va. 20110-2209. The date of the deposits was Jan. 26, 2010. The accession numbers for those deposited seeds of tomato hybrid PS 01565172 and inbred parent lines FDR 15-2081 and FDS 15-2118 are ATCC Accession Number PTA-10609, ATCC Accession Number PTA-10606, and ATCC Accession Number PTA-10607, respectively. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Klee et al., *Bio-Technology*, 3(7):637-642, 1985.

Kuhlemeier et al., *Plant Cell,* 1:471, 1989.
Marcotte et al., *Nature,* 335:454, 1988.
Marcotte et al., *Plant Cell,* 1:969, 1989.
Odel et al., *Nature,* 313:810, 1985.
Omirulleh et al., *Plant Mol. Biol.,* 21(3):415-428, 1993.
Potrykus et al., *Mol. Gen. Genet.,* 199:183-188, 1985.
Roshal et al., *EMBO J.,* 6:1155, 1987.
Schaffner and Sheen, *Plant Cell,* 3:997, 1991.
Schernthaner et al., *EMBO J.,* 7:1249, 1988.
Siebertz et al., *Plant Cell,* 1:961, 1989.
Simpson et al., *EMBO J.,* 4:2723, 1985.
Terada and Shimamoto, *Mol. Gen. Genet.,* 220:389, 1990.
Uchimiya et al., *Mol. Gen. Genet.,* 204:204, 1986.
Wang et al., *Science,* 280:1077-1082, 1998.
Williams et al., *Nucleic Acids Res.,* 1 8:6531-6535, 1990.
WO 99/31248

What is claimed is:

1. A tomato plant comprising at least a first set of the chromosomes of tomato line FDR 15-2081, a sample of seed of said line having been deposited under ATCC Accession Number PTA-10606.

2. A seed comprising at least a first set of the chromosomes of tomato line FDR 15-2081, a sample of seed of said line having been deposited under ATCC Accession Number PTA-10606.

3. The plant of claim 1, which is hybrid.

4. The plant of claim 1, which is hybrid.

5. The seed of claim 2, wherein the seed produces an inbred plant of line FDR 15-2081.

6. A plant part of the plant of claim 1.

7. The plant part of claim 6, further defined as a leaf, an ovule, pollen, a fruit, or a cell.

8. A tomato plant having all the physiological and morphological characteristics of the tomato plant of claim 3.

9. A tissue culture of regenerable cells of the plant of claim 1.

10. The tissue culture according to claim 9, comprising cells or protoplasts from a plant part selected from the group consisting of embryos, meristems, cotyledons, pollen, leaves, anthers, roots, root tips, pistil, flower, seed and stalks.

11. A tomato plant regenerated from the tissue culture of claim 10.

12. A method of vegetatively propagating the plant of claim 1 comprising the steps of:
   (a) collecting tissue capable of being propagated from the plant according to claim 1;
   (b) cultivating said tissue to obtain proliferated shoots; and
   (c) rooting said proliferated shoots to obtain rooted plantlets.

13. The method of claim 12, further comprising growing at least a first plant from said rooted plantlets.

14. A method of introducing a desired trait into a tomato line comprising:
   (a) crossing a plant of line FDR 15-2081 with a second tomato plant that comprises a desired trait to produce F1 progeny, a sample of seed of said line having been deposited under ATCC Accession Number PTA-10606;
   (b) selecting an F1 progeny that comprises the desired trait;
   (c) backcrossing the selected F1 progeny with a plant of line FDR 15-2081 to produce backcross progeny;
   (d) selecting backcross progeny comprising the desired trait and the physiological and morphological characteristics of tomato line FDR 15-2081; and
   (e) repeating steps (c) and (d) three or more times to produce selected fourth or higher backcross progeny that comprises the desired trait.

15. A tomato plant produced by the method of claim 14.

16. A method of producing a plant comprising an added trait, the method comprising introducing a transgene conferring the trait into a plant of line FDR 15-2081, a sample of seed of said line having been deposited under ATCC Accession Number PTA-10606.

17. A plant produced by the method of claim 16.

18. A method of determining the genotype of the plant of claim 1 comprising obtaining a sample of nucleic acids from said plant and detecting in said nucleic acids a plurality of polymorphisms, thereby determining the genotype of the plant.

19. The method of claim 18, further comprising the step of storing the results of detecting the plurality of polymorphisms on a computer readable medium.

20. The plant of claim 1, further comprising a transgene.

21. The plant of claim 20, wherein the transgene confers a trait selected from the group consisting of male sterility, herbicide tolerance, insect resistance, pest resistance, disease resistance, modified fatty acid metabolism, environmental stress tolerance, modified carbohydrate metabolism and modified protein metabolism.

22. A plant of tomato line FDR 15-2081, further comprising a single locus conversion, a sample of seed of said line having been deposited under ATCC Accession Number PTA-10606, wherein said plant contains essentially all of the morphological and physiological characteristics of tomato line FDR 15-2081.

23. The plant of claim 22, wherein the single locus conversion confers a trait selected from the group consisting of male sterility, herbicide tolerance, insect resistance, pest resistance, disease resistance, modified fatty acid metabolism, environmental stress tolerance, modified carbohydrate metabolism and modified protein metabolism.

24. A method for producing a seed of a plant derived from line FDR 15-2081 comprising the steps of:
   (a) crossing a tomato plant of line FDR 15-2081 with itself or a second tomato plant; a sample of seed of said line having been deposited under ATCC Accession Number PTA-10606; and
   (b) allowing seed of a line FDR 15-2081-derived tomato plant to form.

25. The method of claim 24, further comprising the steps of:
   (c) selfing a plant grown from said FDR 15-2081-derived tomato seed to yield additional line FDR 15-2081-derived tomato seed;
   (d) growing said additional line FDR 15-2081-derived tomato seed of step (c) to yield additional line FDR 15-2081-derived tomato plants; and
   (e) repeating the crossing and growing steps of (c) and (d) to generate at least a first further line FDR 15-2081-derived tomato plant.

26. The method of claim 24, wherein the second tomato plant is of an inbred tomato line.

27. The method of claim 25, further comprising:
   (f) crossing the further FDR 15-2081-derived tomato plant with a different tomato plant to produce seed of a hybrid progeny plant.

28. A method of producing a tomato seed comprising crossing the plant of claim 1 with itself or a second tomato plant and allowing seed to form.

29. A method of producing a tomato fruit comprising:
   (a) obtaining the plant according to claim 1, wherein the plant has been cultivated to maturity; and
   (b) collecting a tomato from the plant.

* * * * *

UNITED STATES PATENT AND TRADEMARK OFFICE
CERTIFICATE OF CORRECTION

PATENT NO.         : 8,097,791 B2                                              Page 1 of 1
APPLICATION NO.    : 12/718644
DATED              : January 17, 2012
INVENTOR(S)        : Douglas Heath It is certified that error appears in the above-identified patent and that said Letters Patent is hereby corrected as shown below:

IN THE CLAIMS:

In column 31, claim 3, line 26, delete "hybrid" and insert --inbred--.

Signed and Sealed this
Tenth Day of April, 2012

David J. Kappos
*Director of the United States Patent and Trademark Office*